(12) United States Patent
Kennedy et al.

(10) Patent No.: US 11,134,959 B2
(45) Date of Patent: Oct. 5, 2021

(54) PATIENT MATCHED INSTRUMENT

(71) Applicant: Smith & Nephew, Inc., Memphis, TN (US)

(72) Inventors: Eric S. Kennedy, Memphis, TN (US); Maroun H. Tarsha, Memphis, TN (US); Zachary C. Wilkinson, Germantown, TN (US); Randy C. Winebarger, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 359 days.

(21) Appl. No.: 16/163,373

(22) Filed: Oct. 17, 2018

(65) Prior Publication Data

US 2019/0150951 A1 May 23, 2019

Related U.S. Application Data

(63) Continuation of application No. 14/420,453, filed as application No. PCT/US2013/054278 on Aug. 9, 2013, now abandoned.

(60) Provisional application No. 61/715,565, filed on Oct. 18, 2012, provisional application No. 61/681,455, filed on Aug. 9, 2012.

(51) Int. Cl.
*A61B 17/15* (2006.01)
*A61B 17/17* (2006.01)
*A61B 17/56* (2006.01)

(52) U.S. Cl.
CPC ............ *A61B 17/157* (2013.01); *A61B 17/15* (2013.01); *A61B 17/1764* (2013.01); *A61B 2017/568* (2013.01)

(58) Field of Classification Search
CPC ..... A61B 17/15; A61B 17/154; A61B 17/157; A61B 17/1764; A61B 2017/568
USPC .......................................... 606/87–88, 96–98
See application file for complete search history.

(56) References Cited

U.S. PATENT DOCUMENTS

| 4,787,383 A * | 11/1988 | Kenna ................ A61B 17/154 606/80 |
| 5,408,409 A | 4/1995 | Glassman et al. |
| 6,205,411 B1 | 3/2001 | DiGioia, III et al. |

(Continued)

FOREIGN PATENT DOCUMENTS

| CA | 2814553 A1 | 4/2012 |
| WO | 1998032384 A1 | 7/1998 |

(Continued)

OTHER PUBLICATIONS

Australian Patent Office, Examination Report No. 1 for AU 2013299493 dated Feb. 16, 2017, 3 pages.

(Continued)

*Primary Examiner* — Jessica Weiss
(74) *Attorney, Agent, or Firm* — Troutman Pepper Hamilton Sanders LLP

(57) ABSTRACT

A patient matched instrument is disclosed. The patient matched instrument includes a body having an interior patient matched surface; a cutting slot extending through at least a portion of the body; a first paddle extending from the body; and a second paddle spaced apart from the first paddle and extending from the body; and wherein at least one of the first paddle and the second paddle further comprises a hook.

20 Claims, 17 Drawing Sheets

(56) References Cited

U.S. PATENT DOCUMENTS

| | | | |
|---|---|---|---|
| 2004/0260301 A1* | 12/2004 | Lionberger | A61B 17/155 606/88 |
| 2009/0087276 A1 | 4/2009 | Rose | |
| 2009/0099567 A1* | 4/2009 | Zajac | A61B 17/155 606/79 |
| 2010/0298894 A1 | 11/2010 | Bojarski et al. | |
| 2010/0305575 A1 | 12/2010 | Wilkinson et al. | |
| 2011/0092977 A1 | 4/2011 | Salehi et al. | |
| 2012/0116562 A1* | 5/2012 | Agnihotri | A61B 17/155 700/98 |
| 2012/0203233 A1 | 8/2012 | Yoshida et al. | |
| 2013/0138111 A1 | 5/2013 | Aram et al. | |
| 2013/0211411 A1* | 8/2013 | Tuke | A61B 17/155 606/88 |
| 2013/0296865 A1* | 11/2013 | Aram | A61B 17/1764 606/80 |
| 2014/0066720 A1* | 3/2014 | Wilkinson | A61B 17/157 600/235 |
| 2015/0245844 A1 | 9/2015 | Kennedy et al. | |

FOREIGN PATENT DOCUMENTS

| | | | | |
|---|---|---|---|---|
| WO | 2011056995 A2 | 5/2011 | | |
| WO | 2011106400 A1 | 9/2011 | | |
| WO | 2011106430 A1 | 9/2011 | | |
| WO | WO-2011106400 A1 * | 9/2011 | | A61B 17/157 |
| WO | 2011156748 A2 | 12/2011 | | |
| WO | 2012051542 A2 | 4/2012 | | |
| WO | 2014026083 A1 | 2/2014 | | |

OTHER PUBLICATIONS

Chao et al., Simulation and Animation of Musculosketal Joint System (Nov. 1, 1993), J. Biomechanical Engineering 115(4B): 562-568.

China Patent Office, First Office Action for CN 201380052809 dated Sep. 26, 2016, 18 pages, including English Translation.

Chinese Office Action (Second); State Intellectual Property Office of People's Republic of China; Chinese Patent Application No. 201380052809.2; Aug. 15, 2017; 19 pages.

Chinese Office Action; State Intellectual Property Office of People's Republic of China; Chinese Patent Application No. 201380074293.1; Sep. 5, 2018; 8 pages.

Delp et al., An Interactive Graphics-Based Model of the Lower Extremity to Study Orthopaedic Surgical Procedures (Aug. 1990), IEE Transactions on Biomedical Engineering 37(8): 757-767.

DiGioia et al., An Integrated Approach to Medical Robotics and Computer Assisted Surgery in Orthopaedics (1995), Carnegie Mellon University 106-111.

DiGioia et al., HipNav: Pre-operative Planning and Intra-operative Navigational Guidance for Acetabular Implant Placement in Total Hip Replacement Surgery (Nov. 1995), Preceedings of CAOS '96 1-8.

Dillman et al., Haptic Devices in Medical Applications (Jun. 23, 1999), Institute for Process Control and Robotics, 1st International Workshop, Paris, France, pp. 12-22.

European Patent Office, First Office Action for EP 13827820 dated Dec. 7, 2017, 4 pages.

European Patent Office, Office Action for EP 13827820 dated Jun. 3, 2016, 8 pages.

Freysinger et al., A Passive-Marker-Based Optical System for Computer-Aided Surgery in Otorhinolaryngology: Development and First Clinical Experiences (Feb. 2002), The Laryngoscope 112(2):409.

Harris et al., Experiences with Robotic Systems for Knee Surgery (Mar. 19-22, 1997), Springer-Verlag, London, UK 757-766.

International Search Report and Written Opinion for PCT/US2013/054278 dated Mar. 4, 2014.

O'Toole III et al., Towards More Capable and Less Invasive Robotic Surgery in Orthopaedics (1995), Computer Vision, Virtual Reality and Robotics in Medicine 905: 123-130.

Taylor et al., An Image-Directed Robotic System for Precise Orthopaedic Surgery (Jun. 1994), IEE Transactions on Robotics and Automation 10 (3): 261-275.

Troccaz et al., The Use of Localizers, Robots and Synergistic Devices in CAS (Nov. 21, 2005), First Joint Conference: Computer Vision, Virtual Reality and Robotics in Medical and Medical Robotics and Computer-Assisted Surgery 1205: 725-736.

* cited by examiner

PATIENT MATCHED INSTRUMENT

CROSS-REFERENCE TO RELATED APPLICATIONS

This application is a continuation application of U.S. patent application Ser. No. 14/420,453, filed on Feb. 9, 2015, and titled "Patient Matched Instrument," which is a national stage application of International Application No. PCT/US2013/054278, filed Aug. 9, 2013, which is a PCT International Application of U.S. Patent Application No. 61/681,455 filed on Aug. 9, 2012, and U.S. Patent Application No. 61/715,565, filed Oct. 18, 2012. The disclosure of each application is incorporated by reference in its entirety.

BACKGROUND OF THE INVENTION

1. Field of the Invention

Embodiments of the present invention generally relate to surgical instruments and methods for the treatment of bones or joints, in some instances surgical instruments that are matched to a particular patient's anatomy, are described herein. Also described are methods of designing and using such surgical instruments.

2. Related Art

Conventional patient-matched instruments are provided with large surfaces that are configured to conform to a patient's unique anatomy. Successful surgical outcomes depend on the ability of patient-matched instruments to provide a reproducible, "confident" 3D-fit between the patient-matched instrument and the anatomy that they are designed to rest against. If there is any doubt by an end user that a patient-matched instrument fits well upon repeated engagement with a patient's unique anatomy, or if the instrument appears to fit well with the patient's anatomy in multiple spatial orientations with respect to the anatomy, the instrument is typically discarded, and the surgery is carried out with the use of conventional, non-patient specific instruments.

To date, at least some patient-matched surgical instruments for use in total knee arthroplasty have employed anatomy-contacting surfaces that are substantially "negatives" of distal femoral and proximal tibial articular joint surfaces. The anatomy-contacting surfaces are generally large surface areas that conform in a continuous manner to substantial areas of a patient's anatomy. In some instances, the custom surgical instruments are provided by obtaining 3D image data of the patient's anatomy (e.g., via an MRI scan), segmenting the 3D image data to clearly delineate surfaces of the bony and/or cartilegeneous anatomy from surrounding tissues, converting the segmented data to a computer model via CAD or other software, performing one or more optional secondary processes (e.g., smoothing functions), using a computer model to customize one or more surfaces of an instrument to the patient's anatomy, and manufacturing the custom instrument such that it is adapted to conform to the patient's anatomy in a single spatial orientation.

In at least some current practices, substantially all portions of the joint anatomy shown in each 3D image data slice are segmented and conventional patient-matched instruments are provided with anatomy-contacting portions that contact substantially continuous areas of the patient's anatomy. Such anatomy-contacting portions have large continuous surface areas of contact with the patient's bone and cartilage, and therefore, it is critical that the engineers or automated programs creating the patient-matched instruments maintain a high level of accuracy and precision throughout each step of the entire segmentation process. Even if only one or two points on anatomy-contacting surfaces of a patient-matched instrument are inaccurate, misaligned, or otherwise misrepresent the true unique anatomy of the patient, the patient-matched instrument may not fit well, sit proud, teeter, wobble, or may not fit at all. In such instances, an end user is less likely to use the instrument. In many cases, poor patient-matched instrument fit may be attributed to even a few minor errors in the segmentation process.

SUMMARY OF THE INVENTION

The various embodiments of the present invention described below and shown in the Figures provide a patient matched instrument that is designed to provide improved repeatability and reproducibility over the prior art. The patient matched instrument incorporates design features that encourage consistent placement and accurate placement.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

The accompanying drawings which is this case is a group of sketches prepared by the inventor and, which are incorporated in and form a part of the specification, illustrate the embodiments of the invention and together with the written description serve to explain the principles, characteristics, and features of the invention. In the drawings.

DETAILED DESCRIPTION OF THE EMBODIMENTS

Figure 1:
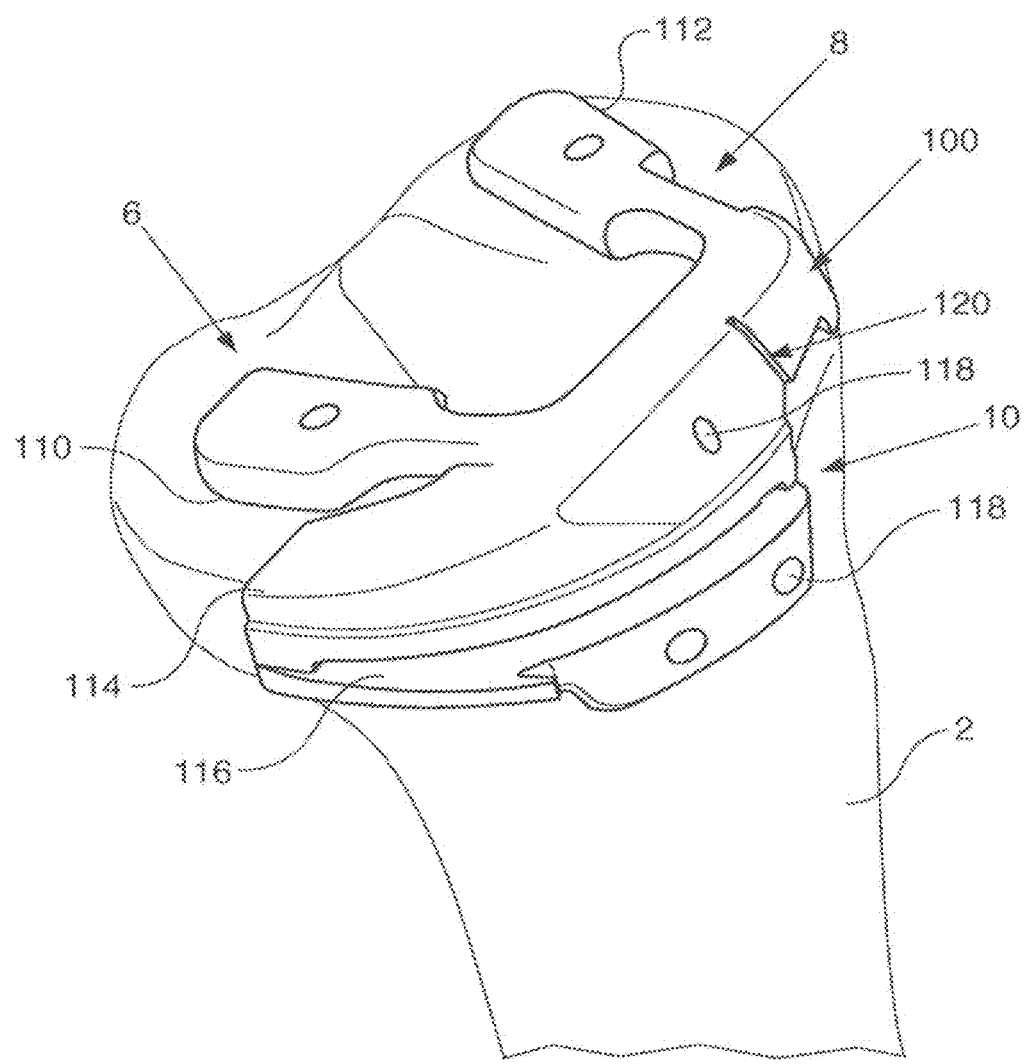
FIG. 1 shows a side perspective view of a patient matched instrument mounted on a left tibia.

Referring to the accompanying drawings in which like reference numbers indicate like elements, FIG. 1 illustrates a patient matched instrument that is designed to provide improved repeatability and reproducibility over the prior art. FIG. 1 illustrates a patient matched (PM) instrument 100 placed on a tibia 2. The patient matched instrument 100 has a first paddle 110, a second paddle 112, a body 114, and a cutting slot 116. The paddles 110, 112 extend from the body 114 and are spaced apart from one another such that the paddles 110, 112 generally contact the medial 6 and lateral 8 tibial condyles. The body 114 may include one or more fixation holes 118. In the depicted embodiment, the body has three fixation holes but any number of holes may be used. The fixation holes 118 are dimensioned to receive pins (not shown) to temporarily fix the patient matched instrument 100 to the tibia 2. The cutting slot 116 is dimensioned to receive a cutting instrument, such as a reciprocating blade (not shown). The body 114 has sufficient depth to provide adequate strength to the cutting slot 116 such that bending of the body and skiving of the cutting instrument may be reduced. In some embodiments, the body 114 includes a groove 120 that may be used for gaging alignment.

In use, the tibia 2 is exposed via surgical incision. The patient matched cutting block 100 is placed on the tibia 2 and located in a home position. Pins (not shown) are inserted into the fixation holes 118. The cutting instrument is reciprocated in the cutting slot 116 to remove bone from a proximal end of the tibia 2.

Figure 2:
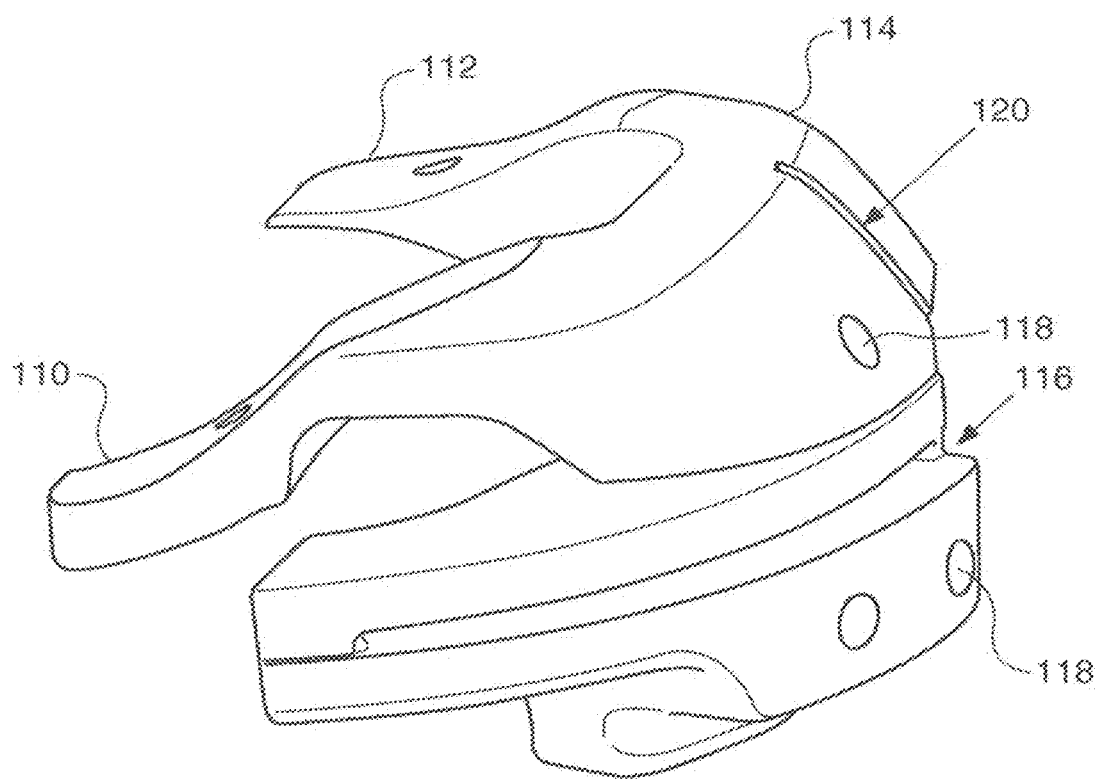
FIG. 2 illustrates a perspective view of the patient matched instrument shown in FIG. 1.

As best seen in FIG. 2, one of the paddles 110, 112 may be thinner or thicker than the other paddle. In the depicted embodiment, the medial paddle has a thickness of about 5 mm. The thickness of the paddles may range from about 2 mm to about 15 mm, and more preferably from about 3 mm to about 5 mm. It is beneficial to the consistent and accurate placement of the PM instrument to minimize unintended potential contact with anatomic structures. For instance, some PM tibia instruments utilize tall or thick proximal paddles with the intent of stiffening the instrument to resist deformation errors, however, the thicker paddles may actually lead to an inability to properly place the PM instrument due to unintended contact between the paddles and one or both femoral condyles. Also, an operator, in attempting to avoid this unintentional contact may alter his or her surgical technique in order to make all femur resections prior to placing the PM tibial instrument. This is a limiting disadvantage because in doing so excludes many techniques that rely on alternating resections on the femur and tibia for the purpose of making resections based on joint balance rather than strictly based on measured resection. By designing the proximal paddles of the PM tibial instrument shorter and by limiting the posterior extent of the paddles, an operator is much more likely to place the instrument with greater accuracy as well as incorporate soft tissue balance techniques into his or her surgical technique. These benefits far outweigh the very small errors associated with deflection of the PM instrument's thinner paddles during placement.

Figure 3:
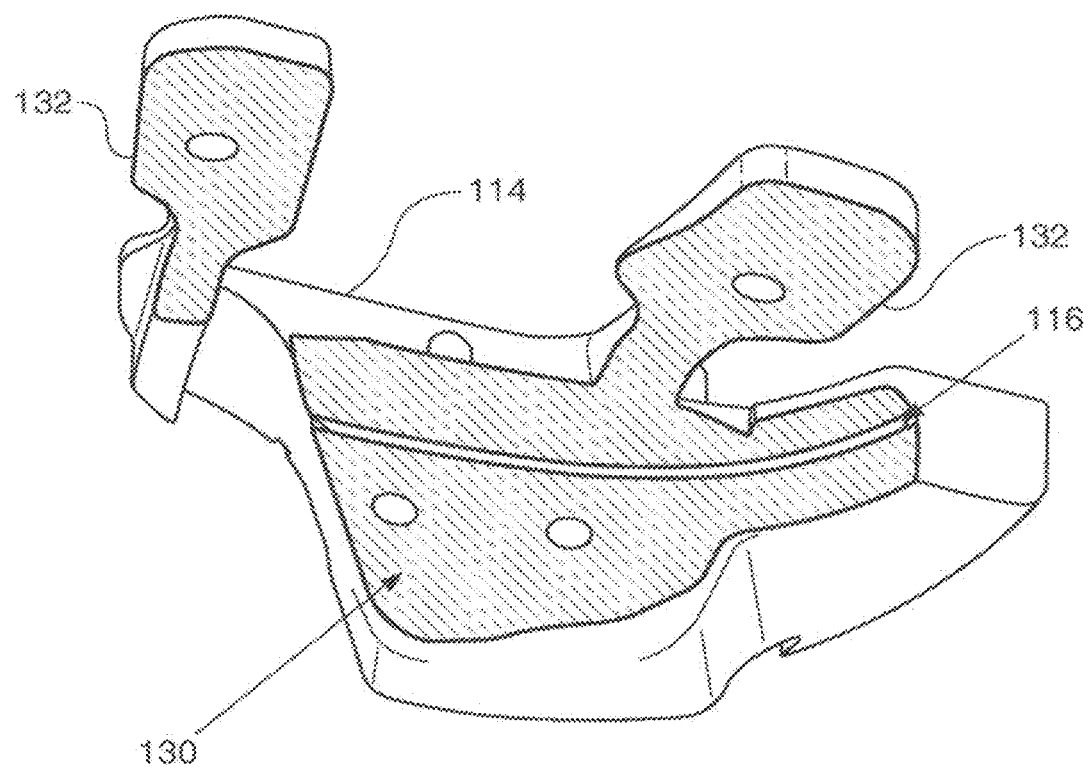
FIG. 3 illustrates a posterior-anterior perspective view of the patient matched instrument shown in FIG. 1.

FIG. 3 illustrates an interior, patient matched surface of the body 130. The patient matched surface 130 contacts an anterior surface 10 of the tibia 2. In the depicted embodiment, the patient matched surface 130 is illustrated using a cross-hatch pattern. This is merely to highlight the area and does not indicate a texture or other surface modification; although, the patient matched area 130 could have a surface roughness different than that of the body 114. In some embodiments, the patient matched surface 130 also contacts the anterior-proximal ridge of the tibia such that the patient matched surface contacts the tibia both superior and inferior of the cutting slot 116. This is significant as the dual contact provides greater repeatability and reproducibility. In addition to the patient matched surface 130, each paddle 110,112 has a contact surface 132. The patient matched surface 130 and the contact surfaces 132 are used to locate the cutting slot 116 relative to the tibia.

Figure 4:
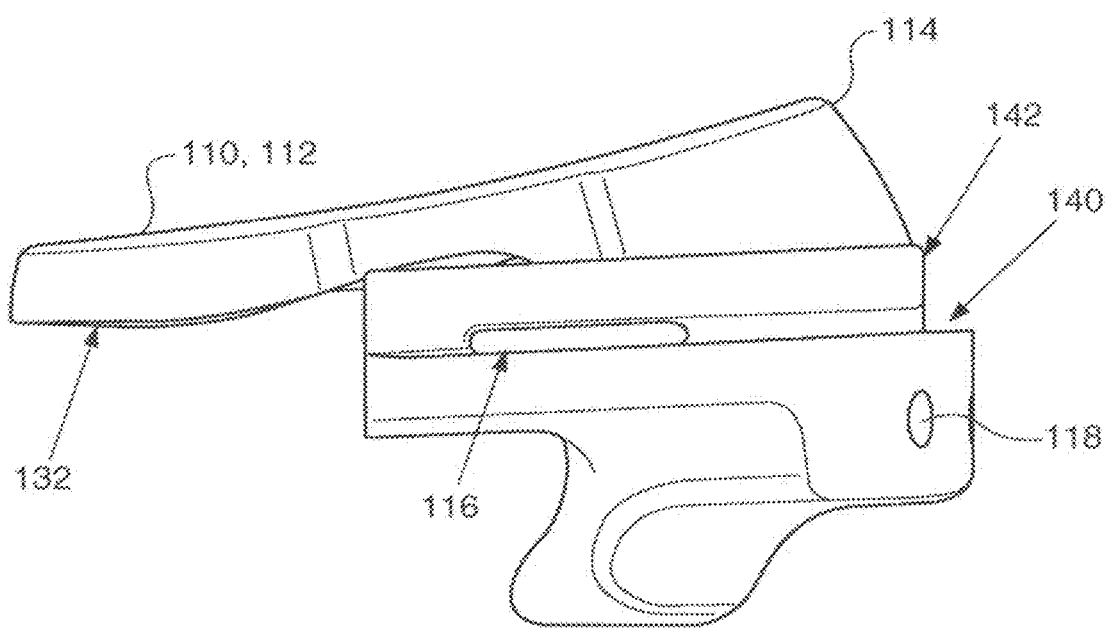
FIG. 4 illustrates a medial-lateral view of the patient matched instrument shown in FIG. 1.

As best seen in FIG. 4, the cutting slot 116 may include a ledge 140. A user may place the cutting instrument on the ledge 140 and use it as a planar guide for cutting. The ledge 140 may extend beyond an exterior surface 142 of the body 114.

Figure 5:
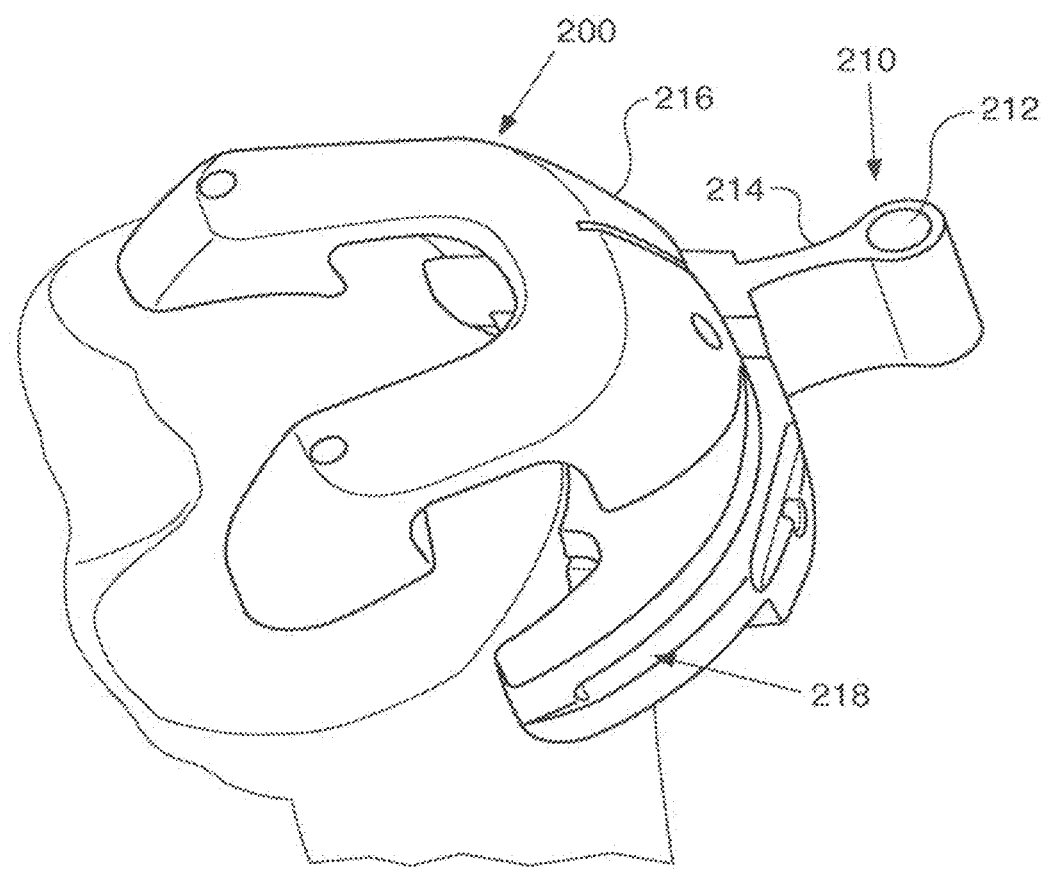
FIG. 5 shows a side perspective view of a patient matched instrument mounted on a left tibia in a second embodiment.
Figure 6:
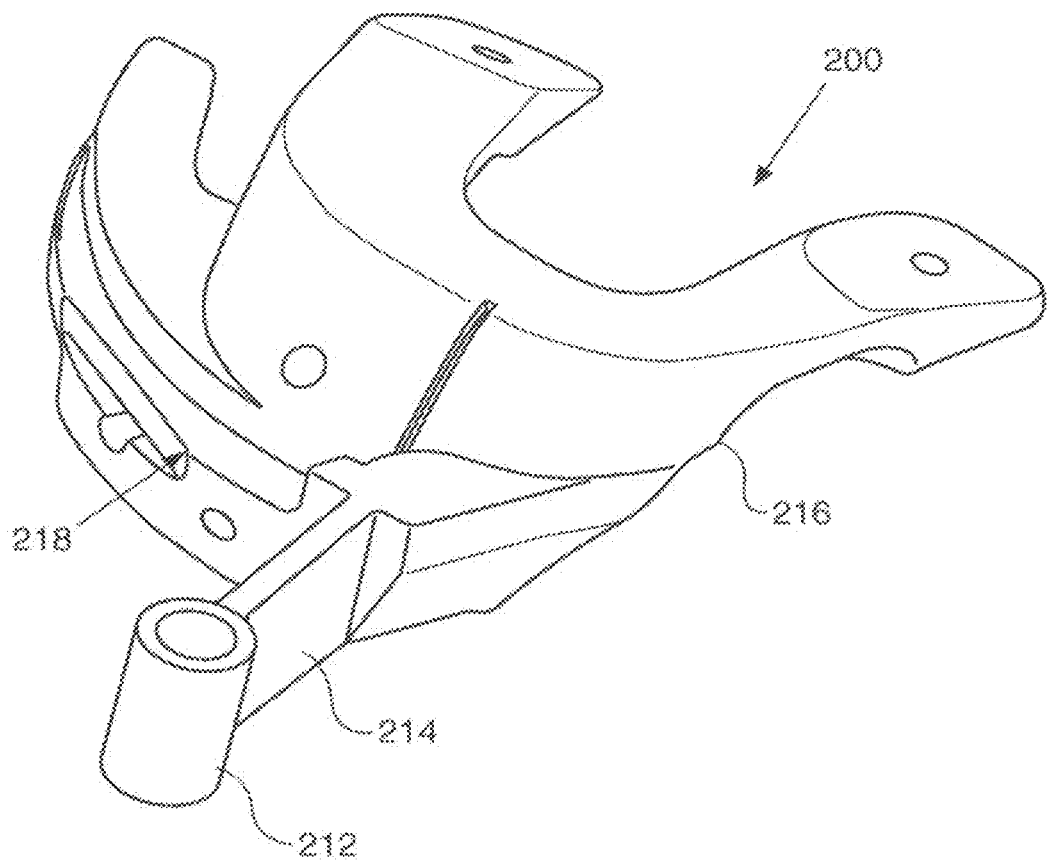
FIG. 6 illustrates a perspective view of the patient matched instrument shown in FIG. 5.

FIGS. 5 and 6 illustrate a second embodiment of the patient matched instrument 200. In this second embodiment, the patient matched instrument 200 includes a built-in alignment checker 210. The built-in alignment checker has a receiver 212 and a bridge 214. The bridge 214 spaces the receiver 212 away from a body 216 of the patient matched instrument 200. A user places a drop rod (not shown) in the receiver 212 to physically check the alignment of a cutting slot 218 before making a cut. Due to the material properties of some PM instruments, the shape of the bridge has a significant functional effect which can be advantageous. In the embodiment shown, the bridge is designed to rigidly constrain the alignment rod (not shown) to the PM instrument in the sagittal plane but to flexibly constrain in the coronal plane. The intent of this particular embodiment is to allow the operator to alter the sagittal alignment (posterior slope) of the PM tibial instrument while greatly reducing the operator's unintentional alteration of the coronal alignment (varus/valgus) of the PM tibial instrument. It has been found that the coronal alignment of the PM block is more consistent than the sagittal alignment. By allowing users to more accurately alter the sagittal alignment with the use of the alignment rod one but minimizing the effect of the alignment rod on the coronal alignment, the bridge shape preserves the inherent consistency of the PM instrument and allows operators to correct for any inconsistency in the sagittal plane. Other embodiments may also be beneficial to other users or with other PM instrument designs, such as a bridge which is shaped to constrain in both sagittal and coronal alignment or a bridge which is shaped to constrain coronal rather than sagittal alignment.

Figure 7:
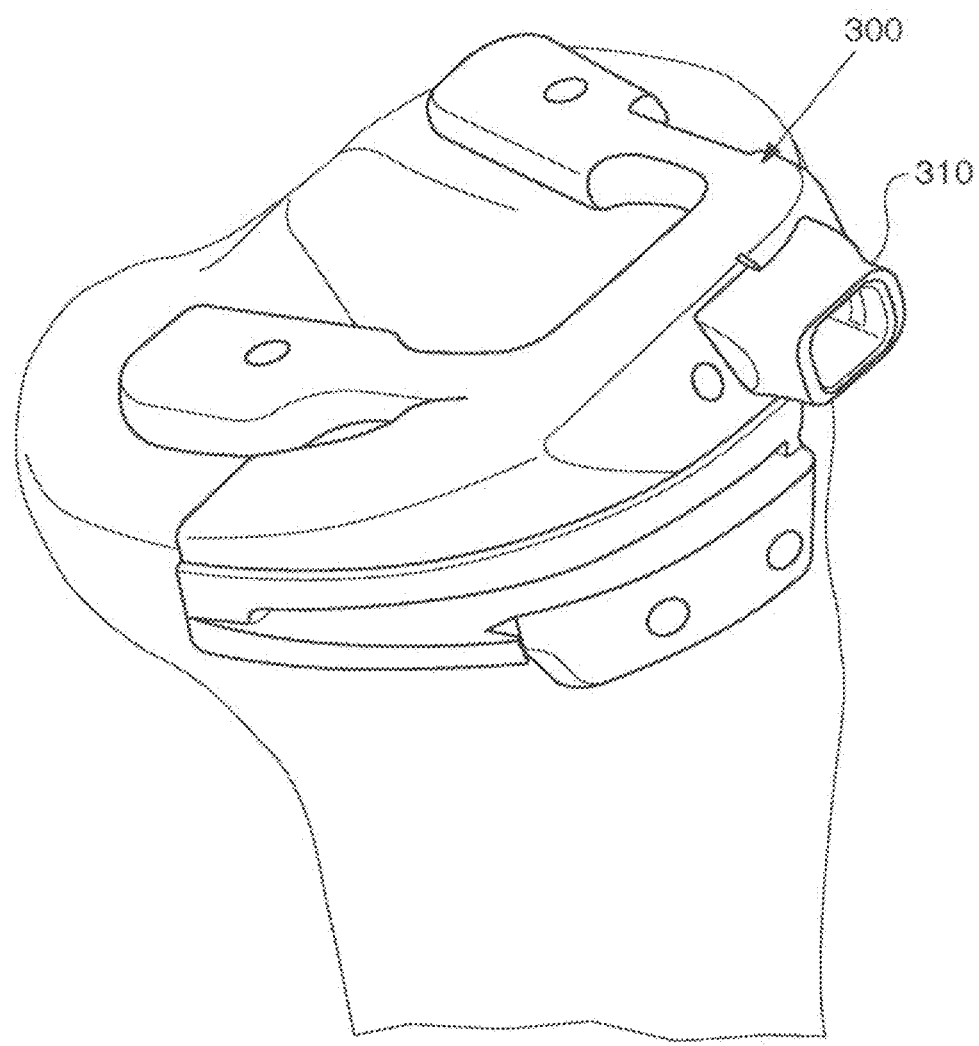
FIG. 7 shows a side perspective view of a patient matched instrument mounted on a left tibia in a third embodiment.

FIG. 7 illustrates a third embodiment of the patient matched instrument 300. In this third embodiment, the patient matched instrument 300 includes a quick connect handle 310. Any number of instruments may be connected to the quick connect handle 310. For example, an alignment checker may be connected to the quick connect handle.

Figure 8:
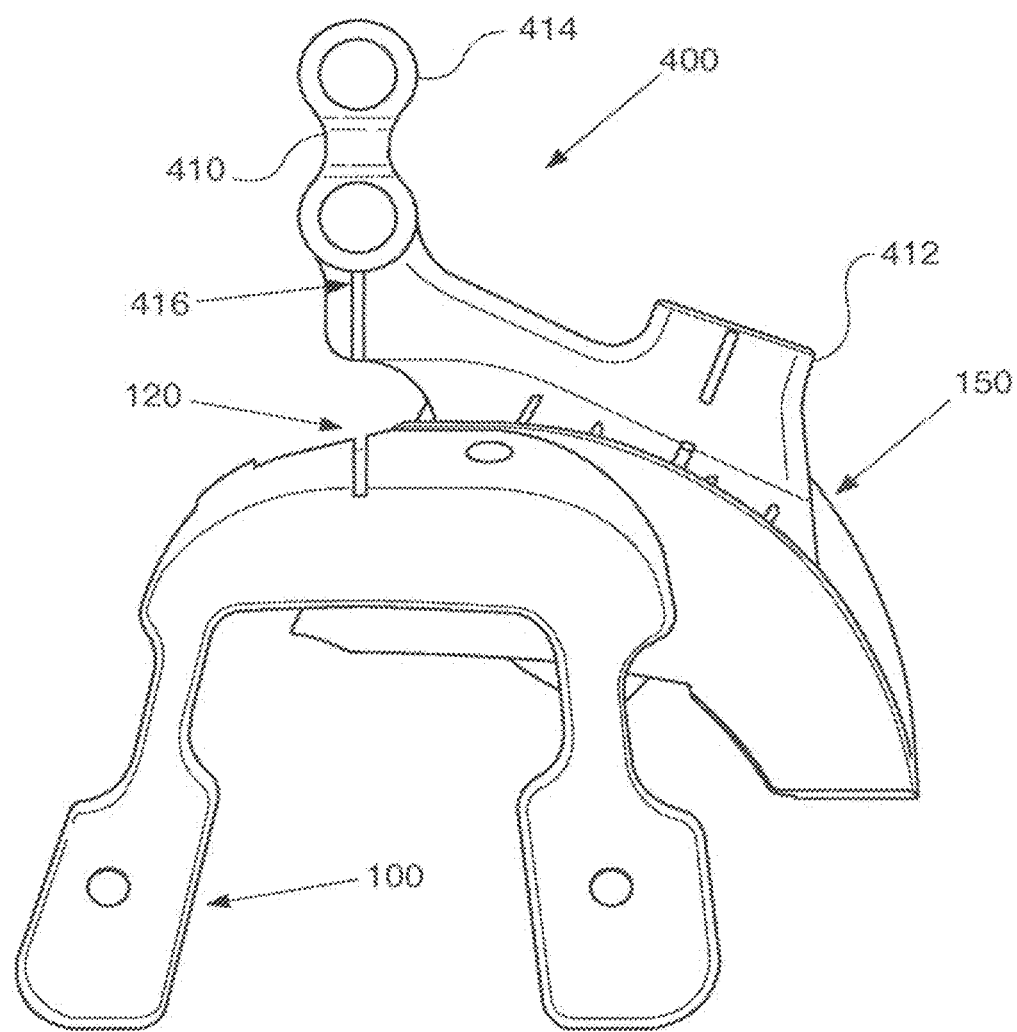
FIG. 8 illustrates a superior-inferior view of a patient matched instrument in a fourth embodiment.

FIG. 8 illustrates an alignment checker guidance tab 400. The alignment checker guidance tab 400 includes a drop rod holder 410 and a quick connect handle 412. The drop rod holder 410 has one or more locations 414 to receive a drop rod (not shown). The alignment checker guidance tab 400 conveniently mates with the patient matched instrument 100 via the cutting slot 116. In some embodiments, the alignment checker guidance tab 400 may include an indentation 416 such that a user can align the groove 120 of the patient matched instrument 100 with the indentation 416 of the alignment checker guidance tab 400.

Figure 9:
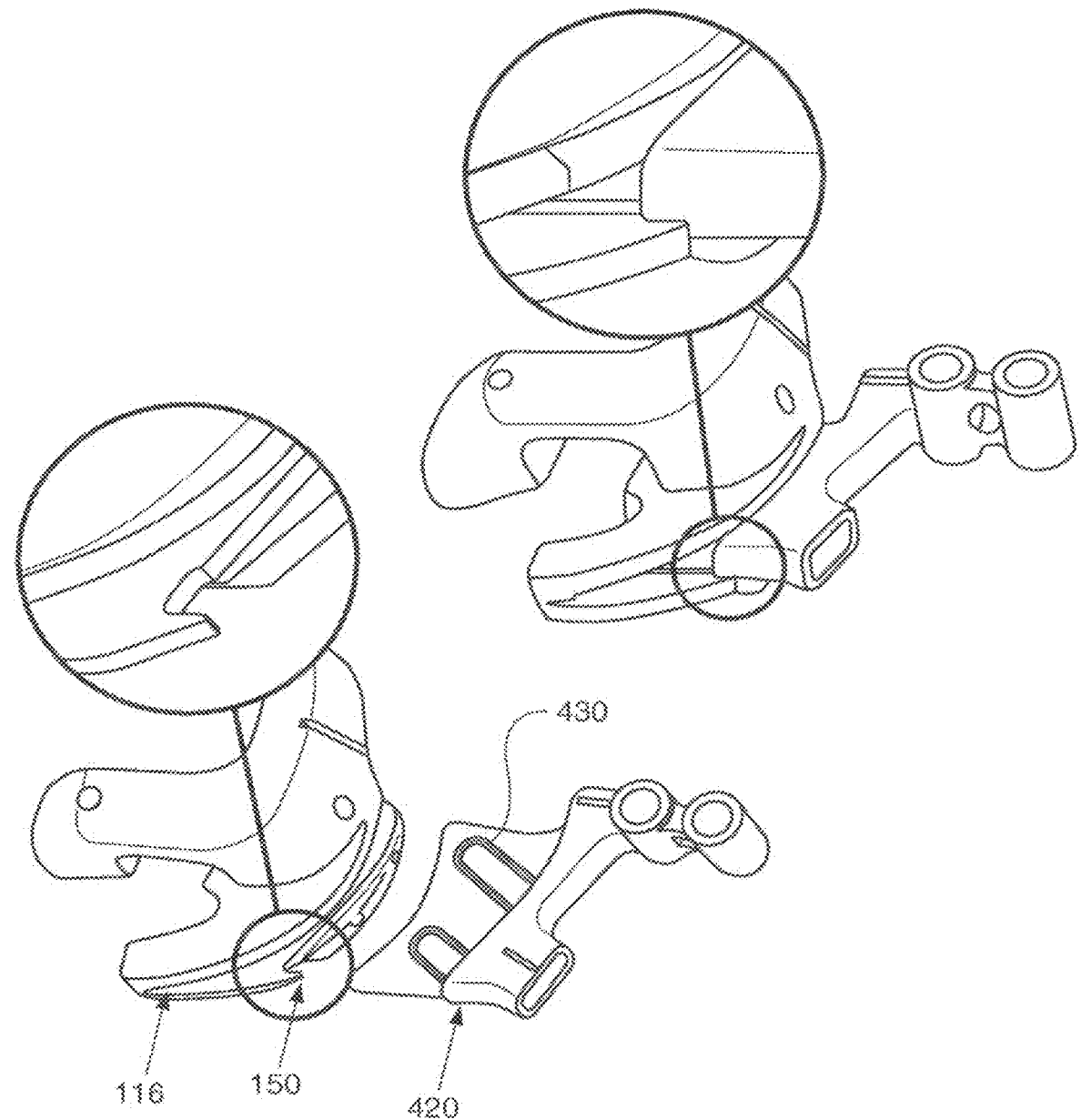
FIG. 9 illustrates detailed views of the patient matched instrument shown in FIG. 8.

As best seen in FIG. 9, the patient matched instrument 100 may include a positive stop 150 for locating the alignment checker guidance tab 400. In the depicted embodiment, the positive stop 150 is a hook-feature that engages a corner 420 of the alignment checker guidance tab 400. The alignment checker guidance tab 400 may include cantilevered tabs or flaps 430. The flaps 430 may engage the cutting slot 116. The flaps 430 may act as a locking mechanism to temporarily lock the alignment checker guidance tab 400 to the patient matched instrument 100 or they may simply frictionally engage the cutting slot 116 to make movement less likely.

Figure 10:
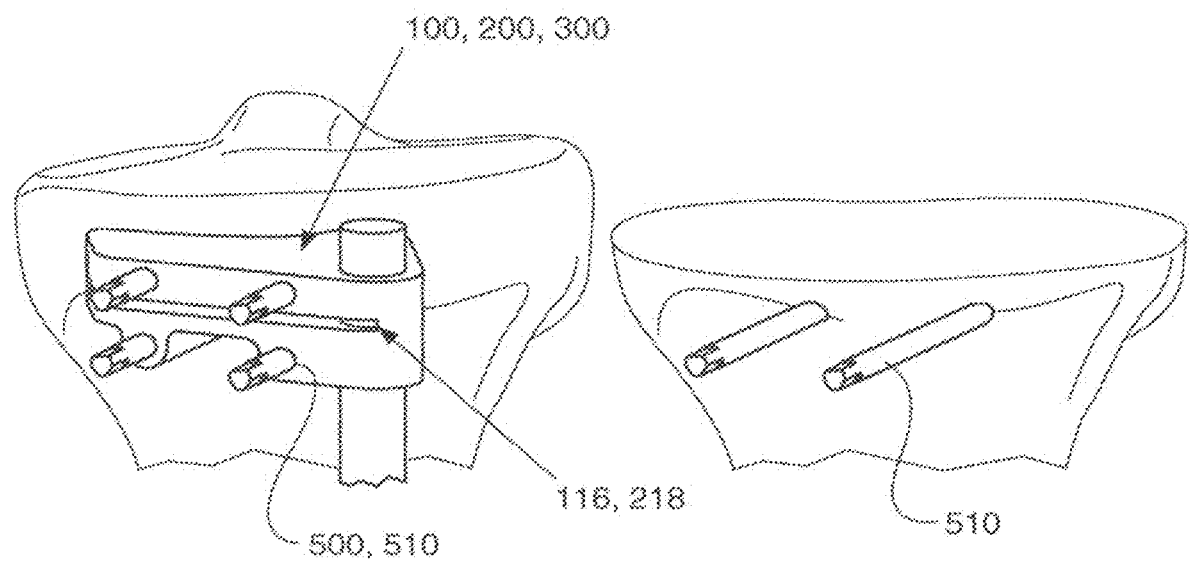
FIG. 10 illustrates pin mounting locations that may be used with any of the above listed embodiments.

FIG. 10 illustrates pin fixation holes 500 and pins 510 for use in conjunction with a patient matched instrument 100, 200, 300. The pin fixation holes 500 may be located both superior and inferior of the cutting slot 116, 218. In the depicted embodiment, four pins are used in four holes but any number of holes and/or pins may be used. Fixation above and below the cutting guide has the effect of reducing resection error due to deformation of the PM instrument when making the resection than a PM instrument without pin fixation above and below the cutting guide.

Figure 11:
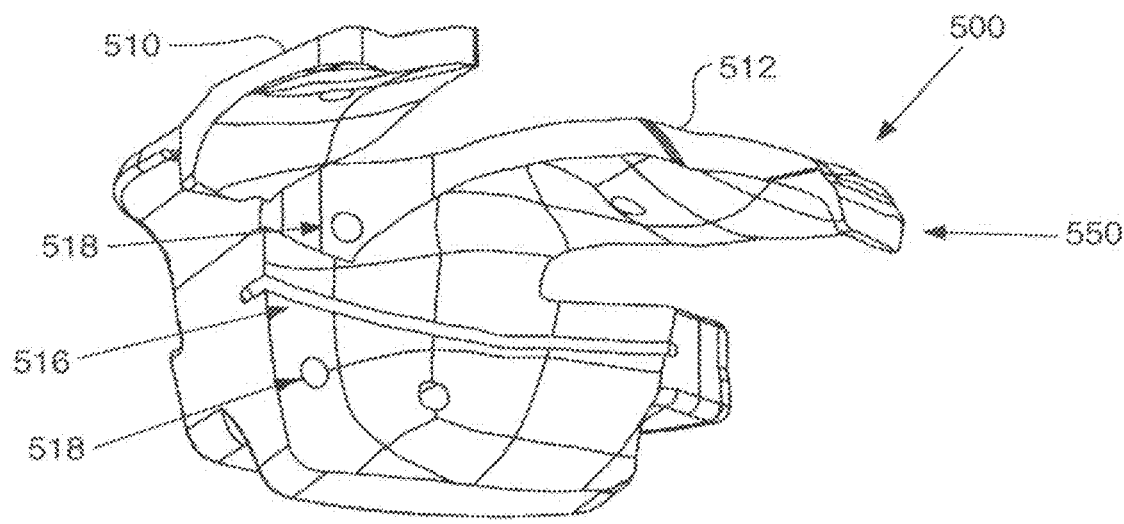
FIG. 11 shows a side perspective view of a patient matched instrument in a fifth embodiment.
Figure 12:
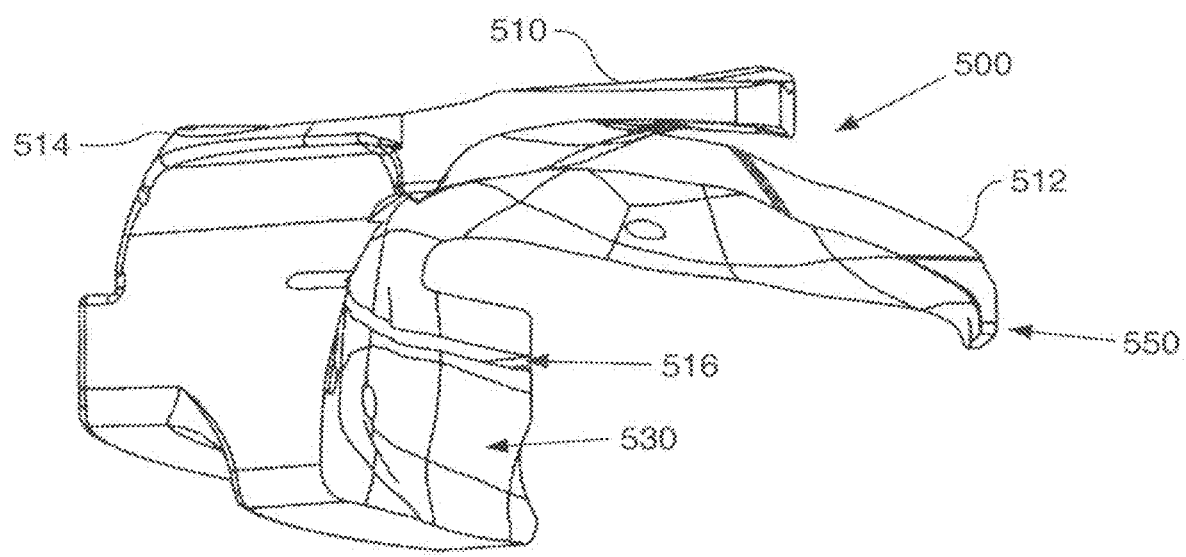
FIGS. 12-15 illustrate a perspective view of the patient matched instrument shown in FIG. 11.

FIG. 11 illustrates a patient matched instrument 500. The patient matched instrument 500 has a first paddle 510, a second paddle 512, a body 514, and a cutting slot 516. The paddles 510, 512 extend from the body 514 and are spaced apart from one another such that the paddles 510, 512 generally contact the medial 6 and lateral 8 tibial condyles. The body 514 may include one or more fixation holes 518. In the depicted embodiment, the body has five fixation holes but any number of holes may be used. The fixation holes 518 are dimensioned to receive pins (not shown) to temporarily fix the patient matched instrument 500 to the tibia 2. The cutting slot 516 is dimensioned to receive a cutting instrument, such as a reciprocating blade (not shown). The body 514 has sufficient depth to provide adequate strength to the cutting slot 516 such that bending of the body and skiving of the cutting instrument may be reduced.

One of the paddles 510, 512 may be thinner or thicker than the other paddle. In the depicted embodiment, both paddles have a thickness of about 4 mm. The thickness of the paddles may range from about 2 mm to about 15 mm, and more preferably from about 3 mm to about 5 mm. Moreover, the paddles 510, 512 may be trimmed at different angles to achieve an overall desired height. The overall height of the paddles 510, 512 may be determined by an offset function relative to the proximal tibia bone surface. Paddles with a sufficient minimum thickness may provide an advantage of allowing for tibial placement prior to making posterior femoral resections.

Figure 13:
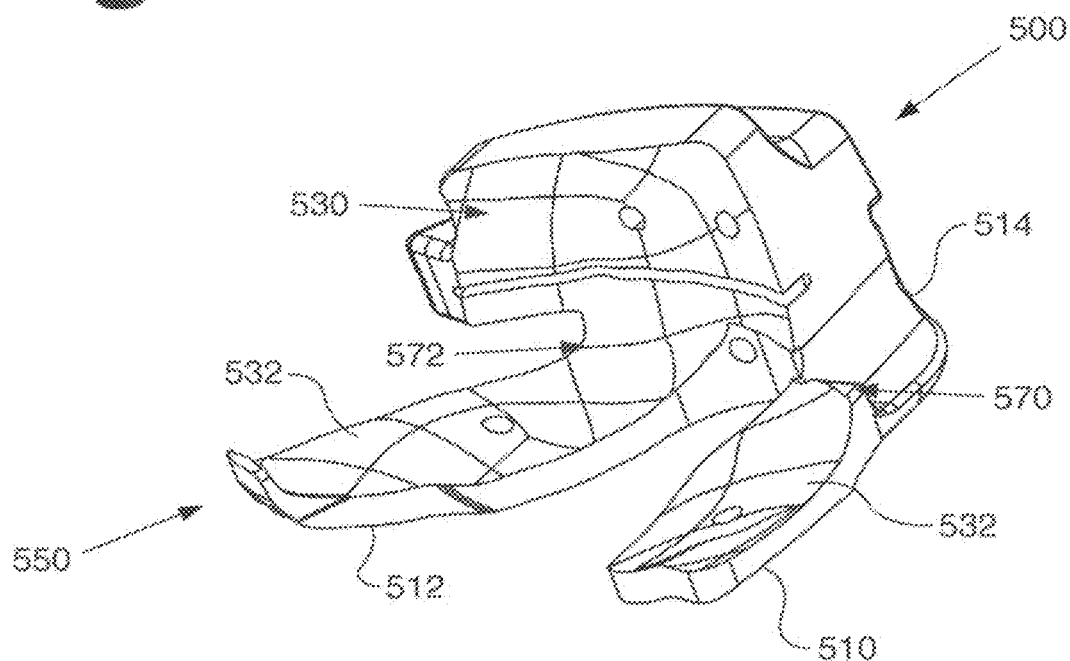
Figure 14:
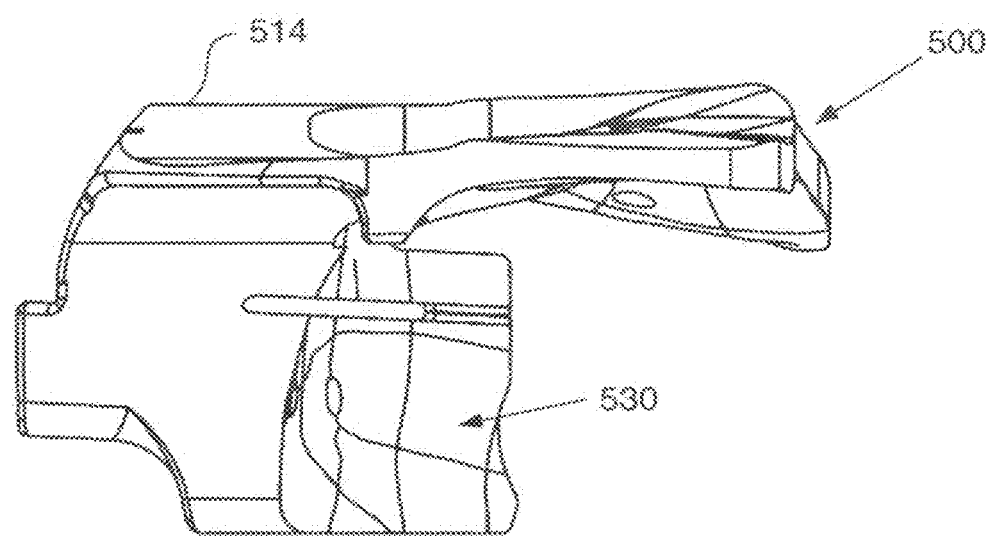
Figure 15:
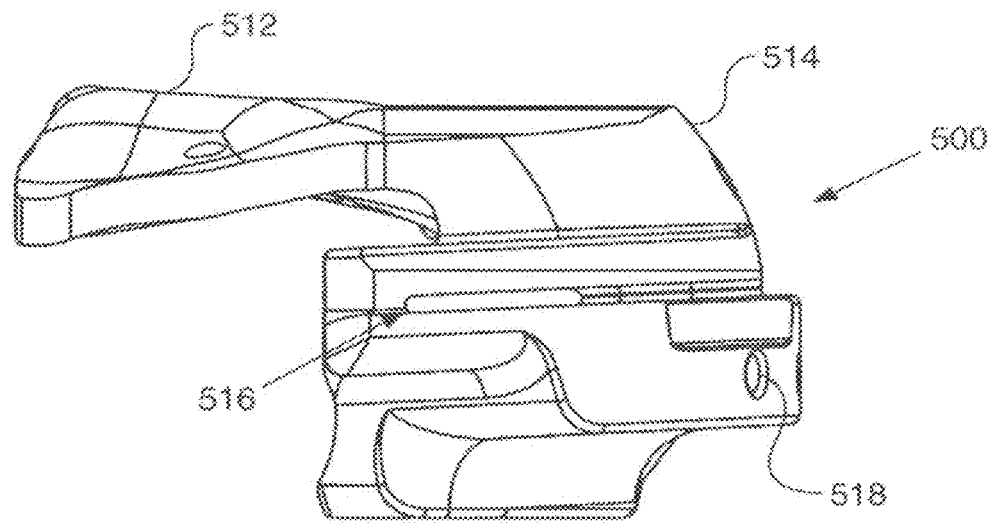
Figure 16:
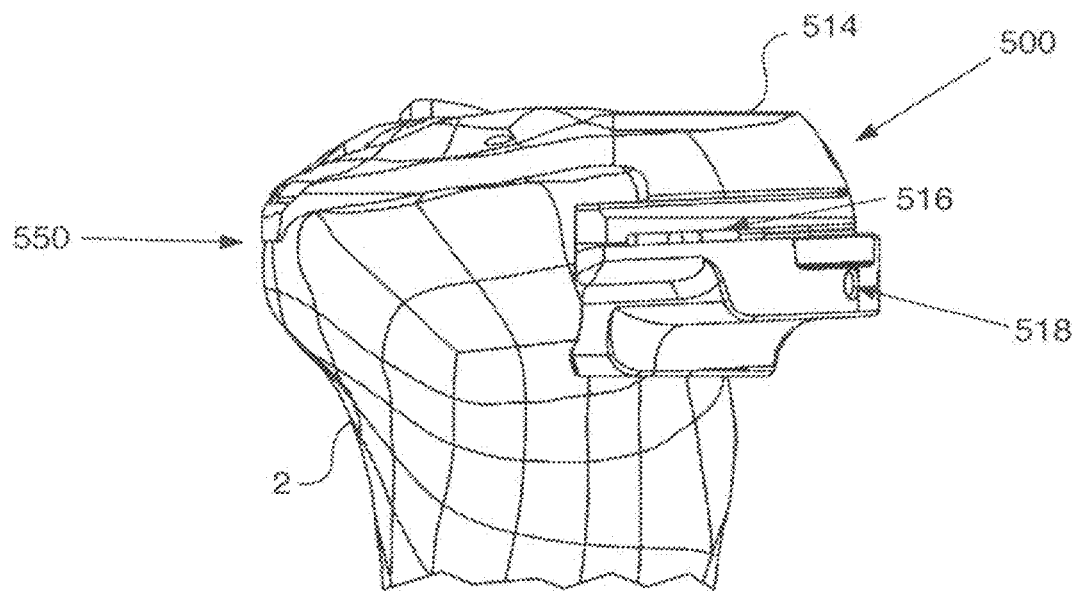
FIGS. 16-18 show the patient matched instrument of FIG. 11 as mounted on a tibia.

As best seen in FIG. 13, the body has an interior, patient matched surface 530. The patient matched surface 530 contacts the anterior surface 10 of the tibia 2. In the depicted embodiment, the patient matched surface 530 is illustrated using a cross-hatch pattern. This is merely to highlight the area and does not indicate a texture or other surface modification; although, the patient matched area 530 could have a surface roughness different than that of the remainder of the body 514. In some embodiments, the patient matched surface 530 also contacts the anterior-proximal ridge of the tibia such that the patient matched surface contacts the tibia both superior and inferior of the cutting slot 516. This is significant as the dual contact provides greater repeatability and reproducibility. In addition to the patient matched surface 530, each paddle 510,512 has a contact surface 532. The patient matched surface 530 and the contact surfaces 532 are used to locate the cutting slot 516 relative to the tibia 2.

FIG. 13 also illustrates an anterior-proximal-lateral tibia body contact portion 570 and an anterior medial contact portion 572.

The patient matched instrument 500 also includes a hook 550. The hook 550 is adapted to contact a posterior surface of the tibia 2. The height and width of the hook 550 may a set size for all patient matched instruments or may be sized based upon a particular patient's anatomy. Although the hook 550 is depicted as being upon the medial paddle, it could also be formed as part of lateral paddle, or both paddles.

Figure 17:
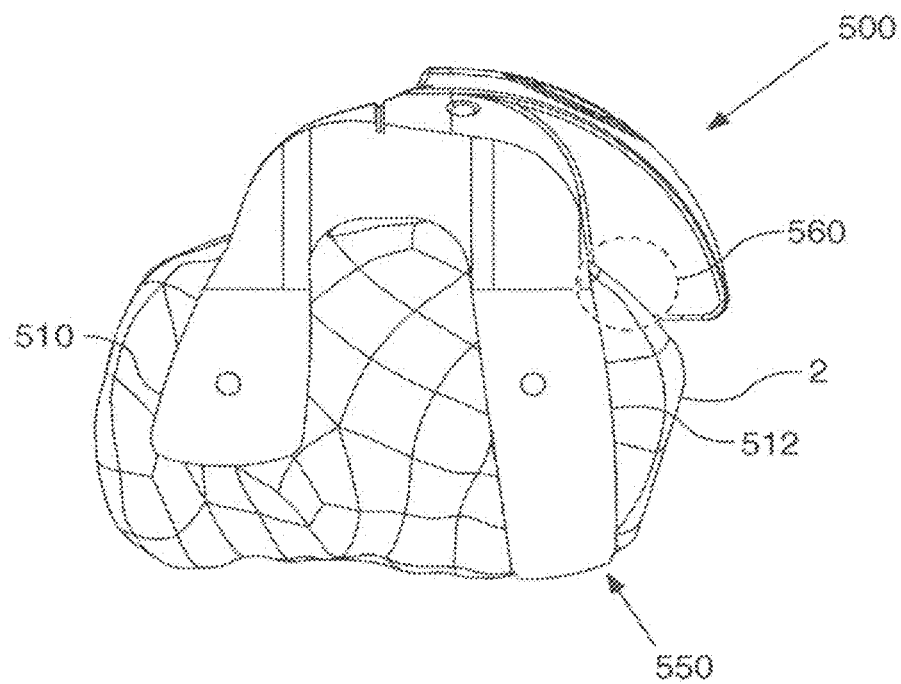
Figure 18:
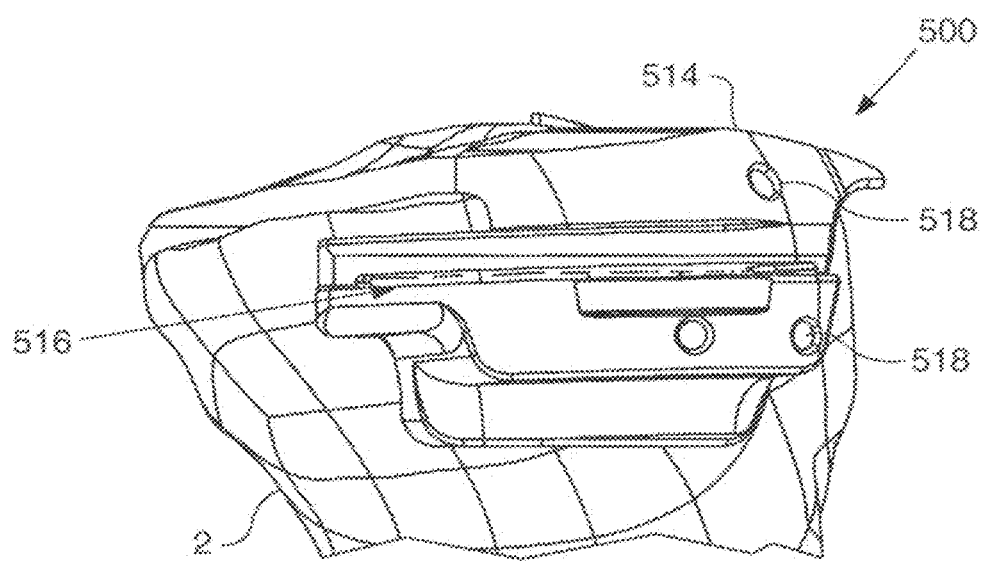

As best seen in FIG. 17, the patient matched instrument 500 includes an area 560 wherein the body 514 is configured to contact a portion of the anterior of the tibia 2 and provides support for the cutting slot 516. The area 560 is matched to the particular patient's anatomy.

In use, the tibia 2 is exposed via surgical incision. The patient matched cutting block 500 is placed on the tibia 2 and located in a home position. Pins (not shown) are inserted into the fixation holes 518. The cutting instrument is reciprocated in the cutting slot 516 to remove bone from a proximal end of the tibia 2.

Figure 19:
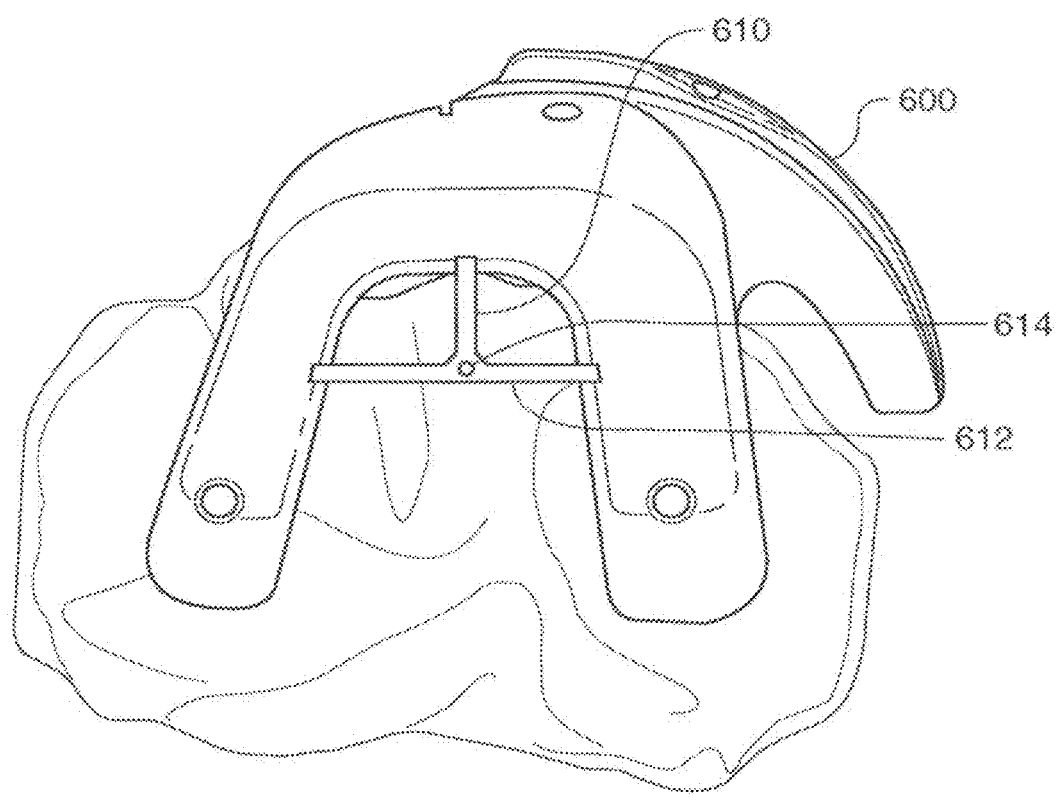
FIG. 19 shows a superior-inferior view of a patient matched instrument in a sixth embodiment.

FIG. 19 yet another embodiment of the patient matched instrument 600. The patient matched instrument 600 includes a confidence point 614, which is formed by the intersection of first member 610 and second member 612. The confidence point may be placed over the ACL attachment point or some other anatomical landmark. Confidence point 614 may be just a visual aid provided by the intersection of members 610, 612 or a hole location. For example, a pin (not shown) may be inserted into the confidence point 614. A user, such as a surgeon, may view the anatomical landmark (e.g., ACL attachment) relative to the confidence point 614.

Figure 20:
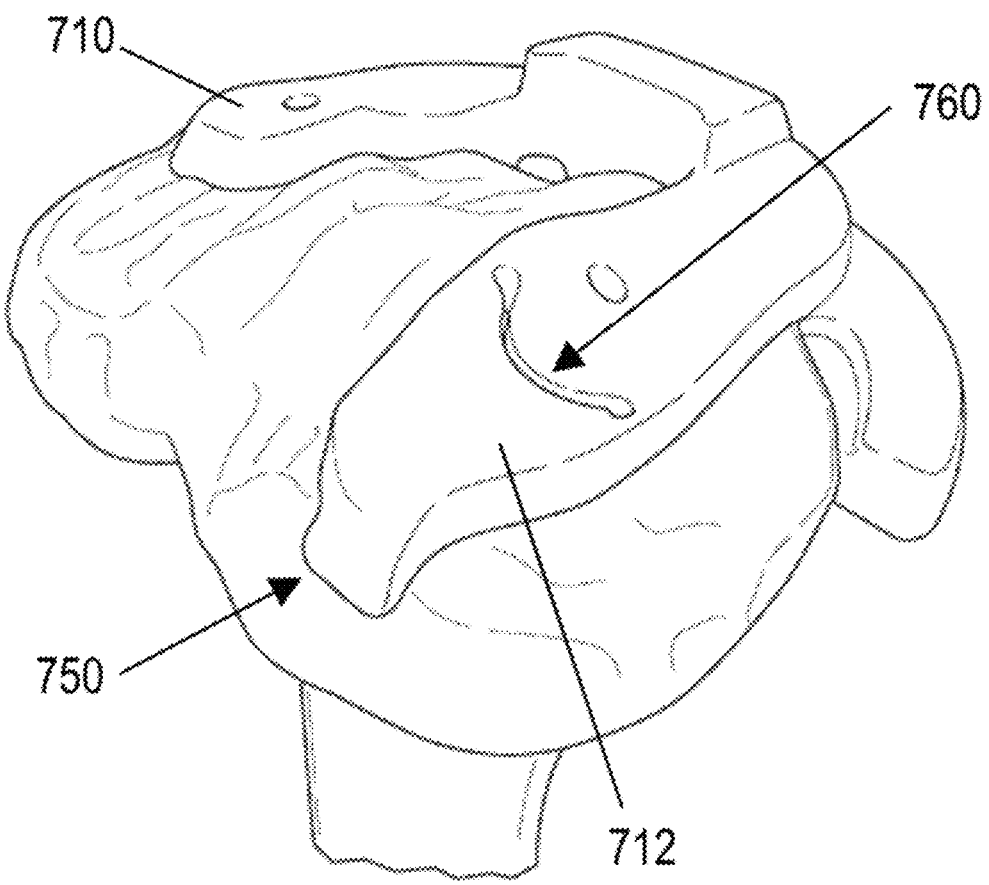
FIG. 20 shows a rear perspective view of a patient matched instrument in a seventh embodiment.
Figure 21:
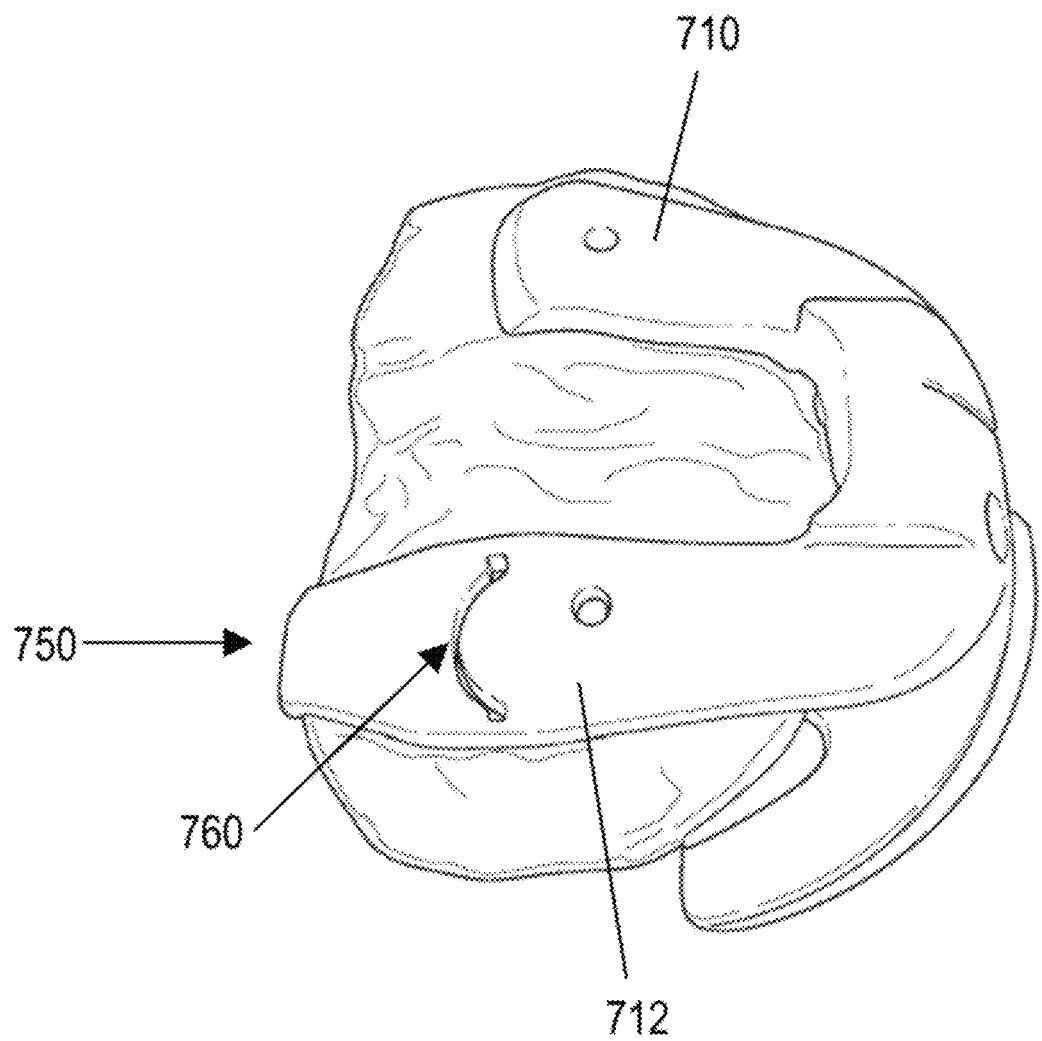
FIG. 21 shows a side perspective view of the patient matched instrument in FIG. 20.

FIG. 20 shows still another embodiment of a patient matched instrument as described herein. The patient matched instrument of FIG. 20 includes paddles 710, 712, along with a hook 750 as described herein. The patient matched instrument of FIG. 20 also includes a removed portion 760 from the paddle 712. FIG. 21 shows an alternative view of the patient matched instrument of FIG. 20, featuring paddles 710, 712, a hook 750, and a removed portion 760 from the paddle 712.

In some embodiments, in order to give a user more confidence in placing a patient matched instrument and/or to minimize the chance of false placement, the patient matched instrument may be provided with certain combined features that act in synergy to enhance the patient matched instrument's fit, stability, and/or constraint. As examples, such features may be larger paddles, anterior medial contact, slot contact, and/or the posterior hook. The location, dimensions, and combinations of particular features may be worked into an algorithm based upon the patient's anatomy and/or user preference. For example, to improve varus/valgus constraint, the features may focus on constraint provided by the medial and lateral paddles. Alternatively, to enhance flexion and extension, the features may focus on constraint provided by the hook and the body along the anterior portion. Otherwise, to enhance rotation, the features may focus on constraint provided by the slot contact and the anterior-proximal-lateral tibia body contact.

Any of the features of the embodiments disclosed herein may be combined in various combinations to form alternative embodiments.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while FIG. 5 illustrates built-in alignment checker, other structure and/or methods may be used to check the alignment of the patient matched instrument. Thus, the breadth and scope of the present invention should not be limited by any of the above-described exemplary embodiments, but should be defined only in accordance with the following claims appended hereto and their equivalents.

What is claimed is:

1. A patient matched instrument comprising:
   a body having an interior patient matched surface;
   a first paddle extending from the body to an end portion of the first paddle; and
   a second paddle spaced apart from the first paddle and extending from the body to an end portion of the second paddle;
   wherein an area of the body is configured to contact an anterior portion of a particular patient's tibia and is matched to the particular patient's anatomy;
   wherein each of the first paddle and the second paddle includes a contact surface positioned between the respective end portions and the body; and
   wherein the end portion of only one of the first paddle and the second paddle further comprises a hook configured to contact a posterior portion of the particular patient's tibia, wherein the hook is matched to the particular patient's anatomy.

2. The patient matched instrument of claim 1, wherein the body further includes at least one fixation hole.

3. The patient matched instrument of claim 1, wherein one of the first paddle and the second paddle is thinner or thicker than the other paddle.

4. The patient matched instrument of claim 1, wherein the interior patient matched surface has a surface roughness different than the remainder of the body.

5. The patient matched instrument of claim 1, further comprising a first member and a second member, and wherein the first member and the second member intersect to provide a confidence point.

6. The patient matched instrument of claim 1, further comprising a built-in alignment checker.

7. The patient matched instrument of claim 6, wherein the built-in alignment checker has a receiver and a bridge.

8. The patient matched instrument of claim 1, wherein the hook has a fixed size.

9. The patient matched instrument of claim 1, wherein the hook is configured to extend inferiorly along the posterior portion of the particular patient's tibia below the contact surface.

10. The patient matched instrument of claim 1, wherein the first paddle is configured to contact only a portion of an articulating surface of a first condyle of the tibia, and wherein the second paddle is configured to contact only a portion of an articulating surface of a second condyle of the tibia.

11. A patient matched instrument configured to be placed on a tibia of a particular patient, the patient matched instrument comprising:
    a body having an interior patient matched surface, wherein the interior patient matched surface is matched to an anterior surface of the tibia;
    a first paddle extending from the body to an end portion of the first paddle; and
    a second paddle spaced apart from the first paddle and extending from the body to an end portion of the second paddle;
    wherein the end portion of only one of the first paddle and the second paddle is a hook configured to engage a posterior surface of the tibia when the interior patient matched surface is configured to be in contact with the anterior surface of the tibia, and wherein the hook is matched to the particular patient's anatomy.

12. The patient matched instrument of claim 11, wherein the end portion of the first paddle includes the hook.

13. The patient matched instrument of claim 12, wherein the first paddle further includes a first contact surface configured to contact a first condyle of the tibia, and wherein the first contact surface is positioned between the hook and the body.

14. The patient matched instrument of claim 13, wherein the second paddle includes a second contact surface configured to contact a second condyle of the tibia, and wherein the patient matched instrument is configured to be placed on the tibia with the interior patient matched surface contacting the anterior surface of the tibia, the hook contacting the posterior surface of the tibia, the first contact surface contacting the first condyle, and the second contact surface contacting the second condyle.

15. A patient matched instrument configured to be placed on a tibia of a particular patient, the tibia having a first bone surface, a first condyle, an opposite second bone surface, and a second condyle, the patient matched instrument comprising:
    a body having an interior patient matched surface matched to the first bone surface of the particular patient;
    a first paddle extending from the body to an end portion of the first paddle, the first paddle including a first contact surface configured to contact the first condyle between the first bone surface and the second bone surface when the interior patient matched surface of the body is configured to be in contact with the first bone surface; and
    a second paddle spaced apart from the first paddle and extending from the body to an end portion of the second paddle, the second paddle including a second contact surface configured to contact the second condyle between the first bone surface and the second bone surface when the interior patient matched surface of the body is configured to be in contact with the first bone surface;

wherein the end portion of only one of the first paddle and the second paddle comprises a hook configured to contact the second bone surface when the interior patient matched surface of the body is configured to be in contact with the first bone surface, and wherein at least one dimension of the hook is sized based on the particular patient's anatomy.

16. The patient matched instrument of claim 15, wherein the first bone surface is an anterior surface of the tibia, and wherein the second bone surface is a posterior surface of the tibia.

17. The patient matched instrument of claim 16, wherein the interior patient matched surface and the hook are configured such that when the instrument is placed on the tibia, the interior patient matched surface and the hook cooperate to limit anterior-posterior movement of the instrument relative to the tibia.

18. A patient matched instrument comprising:
a body having an interior patient matched surface;
a first paddle extending from the body to an end portion of the first paddle; and
a second paddle spaced apart from the first paddle and extending from the body to an end portion of the second paddle;
wherein an area of the body is configured to contact an anterior portion of a particular patient's tibia and is matched to the particular patient's anatomy; and
wherein the end portion of only one of the first paddle and the second paddle further comprises a hook configured to contact a posterior portion of the particular patient's tibia, wherein the hook is matched to the particular patient's anatomy.

19. The patient matched instrument of claim 18, wherein the hook has a fixed size.

20. The patient matched instrument of claim 18, wherein the hook is configured to extend inferiorly along the posterior portion of the particular patient's tibia.

* * * * *